US010456785B2

(12) United States Patent
Daniels et al.

(10) Patent No.: US 10,456,785 B2
(45) Date of Patent: Oct. 29, 2019

(54) METHOD AND APPARATUS FOR REMOTE IDENTIFICATION AND MONITORING OF AIRBORNE MICROBIAL ACTIVITY

(71) Applicant: Nuwave Sensor Technology Limited, Dublin (IE)

(72) Inventors: Stephen Daniels, Dublin (IE); Shane Phelan, Durrow (IE); Ruairi Monaghan, Swords (IE)

(73) Assignee: NUWAVE SENSOR TECHNOLOGY LIMITED, Dublin (IE)

( * ) Notice: Subject to any disclaimer, the term of this patent is extended or adjusted under 35 U.S.C. 154(b) by 102 days.

(21) Appl. No.: 15/410,861

(22) Filed: Jan. 20, 2017

(65) Prior Publication Data

US 2017/0209860 A1 Jul. 27, 2017

(30) Foreign Application Priority Data

Jan. 21, 2016 (GB) .................................. 1601161.1

(51) Int. Cl.

| | |
|---|---|
| *B01L 3/00* | (2006.01) |
| *C12M 1/00* | (2006.01) |
| *C12M 1/04* | (2006.01) |
| *C12M 3/00* | (2006.01) |
| *C12M 1/26* | (2006.01) |
| *C12M 1/34* | (2006.01) |
| *G01N 21/51* | (2006.01) |
| *G01N 21/47* | (2006.01) |

(52) U.S. Cl.

CPC ............ *B01L 3/508* (2013.01); *C12M 23/22* (2013.01); *C12M 23/24* (2013.01); *C12M 23/42* (2013.01); *C12M 31/10* (2013.01); *C12M 33/00* (2013.01); *C12M 41/46* (2013.01); *G01N 21/51* (2013.01); *B01L 2200/10* (2013.01); *B01L 2300/021* (2013.01); *B01L 2300/023* (2013.01); *B01L 2300/027* (2013.01); *B01L 2300/0654* (2013.01); *G01N 2021/4707* (2013.01); *G01N 2021/4709* (2013.01)

(58) Field of Classification Search

None

See application file for complete search history.

(56) References Cited

U.S. PATENT DOCUMENTS

| | | | | |
|---|---|---|---|---|
| 3,956,070 | A | 5/1976 | Kenyon | |
| 7,175,762 | B1 * | 2/2007 | Noca | B01D 39/2055 204/450 |
| 2004/0232052 | A1 * | 11/2004 | Call | B01D 21/2455 209/143 |
| 2006/0017230 | A1 | 1/2006 | Hirleman et al. | |

FOREIGN PATENT DOCUMENTS

| | | | |
|---|---|---|---|
| AU | 642878 | B2 | 11/1993 |
| WO | 01/83673 | A2 | 11/2001 |

OTHER PUBLICATIONS

Search report for Great Britain Patent Application No. GB1601161.1 dated Oct. 26, 2016.

* cited by examiner

*Primary Examiner* — Blaine Lankford

(74) *Attorney, Agent, or Firm* — Bishop, Diehl & Lee, Ltd.

(57) ABSTRACT

An optical sensor and airborne pathogen proliferation assembly for remote, optical detection and monitoring of pathogens is disclosed.

13 Claims, 4 Drawing Sheets

METHOD AND APPARATUS FOR REMOTE IDENTIFICATION AND MONITORING OF AIRBORNE MICROBIAL ACTIVITY

CROSS-REFERENCE TO RELATED APPLICATIONS

This application claims the benefit of Great Britain Patent Application Serial No. 1601161.1 filed on Jan. 21, 2016.

TECHNICAL FIELD

The present invention relates to an apparatus and method for remote identification and monitoring of microbial activity. More specifically, the invention relates to an assembly comprising: at least one light source; two or more optical detectors; a housing facilitating the placement of an optically transparent container for microbial growth media through which the light source may pass; and an electronic circuit to control the illumination of the growth media container and facilitate transmission and storage of signals detected by the optical detectors.

BACKGROUND

In food, healthcare and agricultural industries, microbial contamination can result in serious disease outbreaks and mass food spoilage ultimately leading to increased mortality, illnesses and costs.

Microbial contaminants may be spread by various means e.g. direct transmission from contaminated surfaces or individuals by touch or through contaminated water supplies. However, in the aforementioned industries even with strict decontamination methods for surfaces, individuals and water supplies in place, microbial contamination still remains commonplace. An aspect of microbial contamination which is far more difficult to control is that of airborne contamination. Microbes may persist on hard to reach surfaces for up to several months or more. When disturbed, these microbes become airborne, enabling transmission to other areas of the particular facility in question. Furthermore, poor compliance with cleaning procedures and high footfall in other areas of a facility may result in regions of high levels contamination. Again, as this area is disturbed by the movement of individuals or machinery, microbial contamination from a low risk' (e.g. warehouse) to a 'high risk' (e.g. food production line) area, through airborne contaminants, is likely.

Current methods for assessing the levels of microbial contamination involve the use of (a) sampling and plating, (b) biochemical laboratory analysis and (c) optical methods.

Assessments using methods (a) and (b) usually involve relatively long timescales (several days), dedicated highly trained staff or investment in costly instrumentation and chemicals, or both. For example, samples must be prepared by an individual skilled in the field of microbiology before growing on nutrient media and enumeration or, in the case of polymerase chain reaction (PCR), samples must be isolated and one or a series of chemical preparations performed before the microbes are identified. Therefore, such methods are usually invoked in very specific laboratory analyses.

Prior art proposes the use of optical techniques for the rapid identification of airborne microbes. For example, US patent publication no. 2003/0098422 A1 proposes the use of a UV laser light source to induce auto-fluorescence of compounds in airborne biological matter. However, coherent sources of UV radiation are rather costly and the capacity of these sources to discern differences in signals emitted from bacteria and moulds requires one or more of more complicated equipment, signal processing techniques, or both. It is appreciated that a less costly approach, using widely available technologies and with increased selectivity, represents an attractive alternative to such methods.

Existing optical methods for determining the presence of microbes in optically transparent solids or fluids use the properties of light scattering by microbial species present in the media. For example, US patent publication no. U.S. Pat. No. 6,107,082A discloses an apparatus and process for automated detection of bacteria in a fluid through measurement of the changes in optical density or turbidity of the medium. However, the process requires several preparatory steps which are most suited to supervised laboratory analyses.

U.S. Pat. No. 7,465,560B2 discloses a rapid bacterial detection method based on light scattering by bacterial colonies. The samples are prepared on growth medium and placed in the optical path of a light source. Detectors measure the pattern and intensity of the forward scattered light and the bacterial species are identified by analysis of the unique "fingerprint" of the forward scattered light patterns. However, there is no method proposed for rapid identification of other microbes, for example moulds, or for automatically sampling from the environment.

Prior art demonstrates the applicability of optical scattering methods for rapid identification of microbes. Given the relative simplicity of such methods it is desirable to apply said methods to a fully automated monitoring device, capable of remote sampling and monitoring in, for example, a food production or healthcare facility. Accordingly, the teachings in this document present a viable device for remote sampling and monitoring of microbial activity suitable for use in ambient monitoring applications.

SUMMARY OF INVENTION

Accordingly the present teaching provides an apparatus for remote sampling and monitoring of microbial activity as detailed in claim 1. Advantageous embodiments are provided in the dependent claims. A method is also provided.

BRIEF DESCRIPTION OF THE DRAWINGS

The present application will now be described with reference to the accompanying drawings in which.

DETAILED DESCRIPTION OF PREFERRED EMBODIMENT(S)

Figure 1:
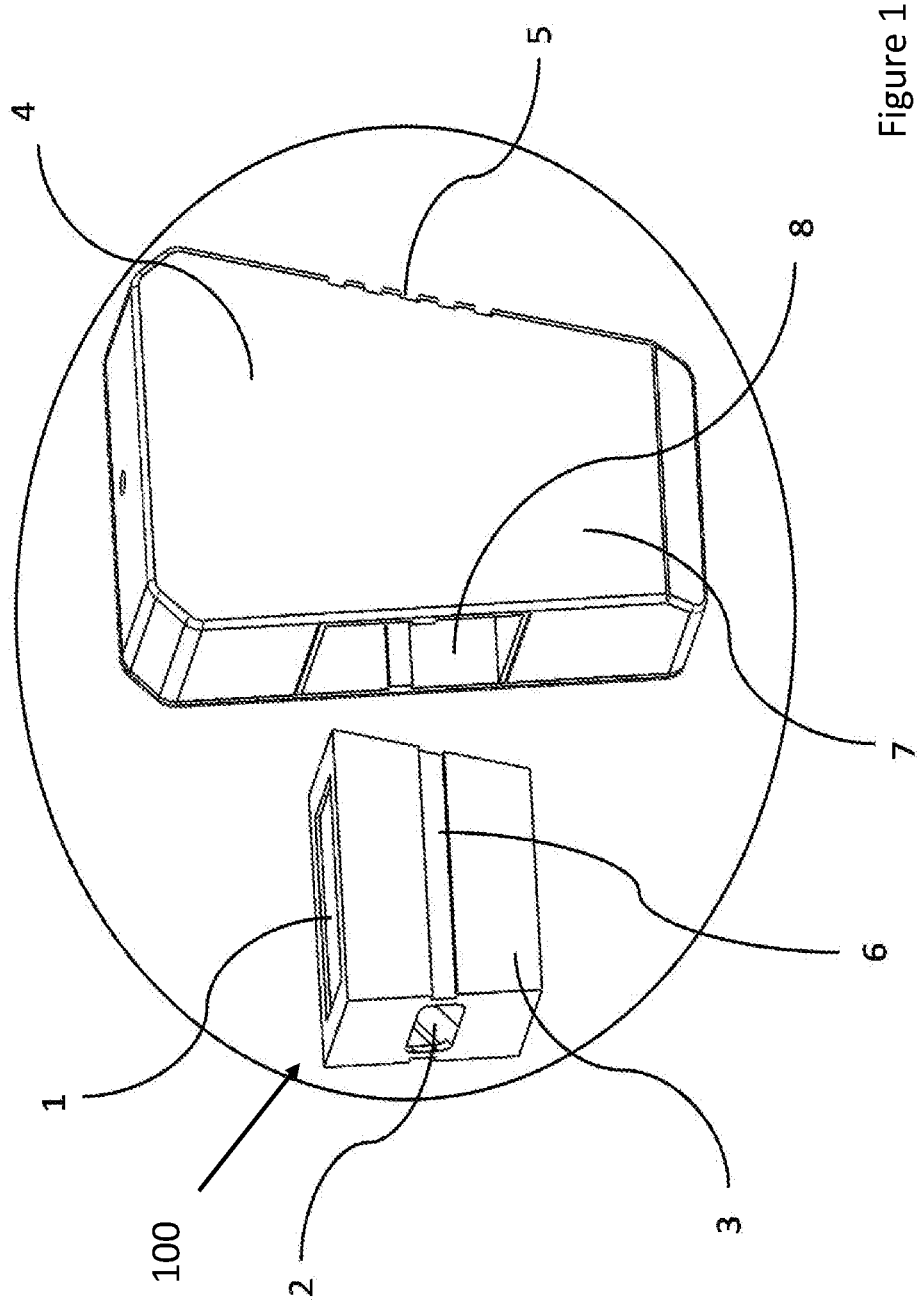
FIG. 1 is a perspective view of airborne microbial growth and detection apparatus.
Figure 2:
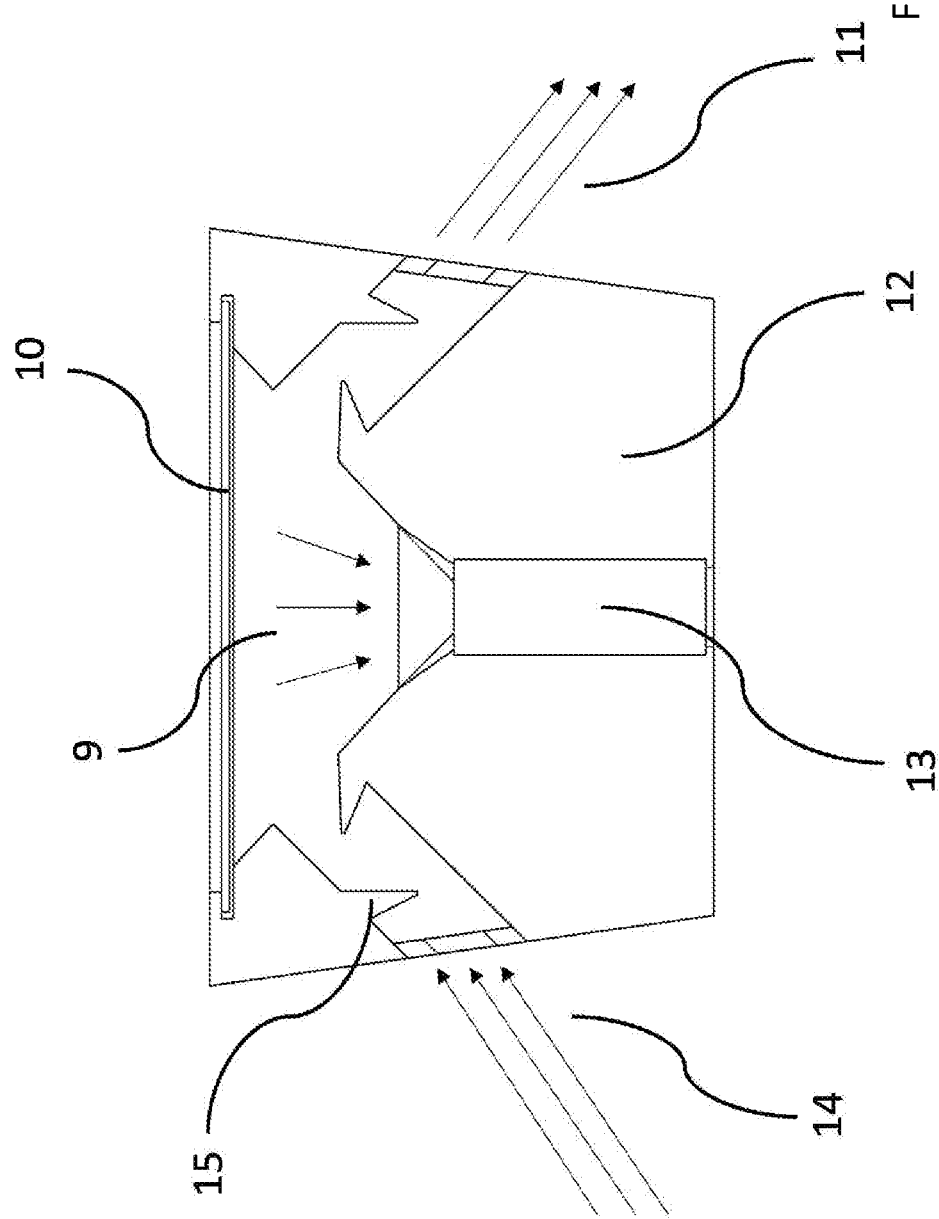
FIG. 2 is a section view through a cartridge component of the airborne microbial growth and detection apparatus of FIG. 1.
Figure 3:
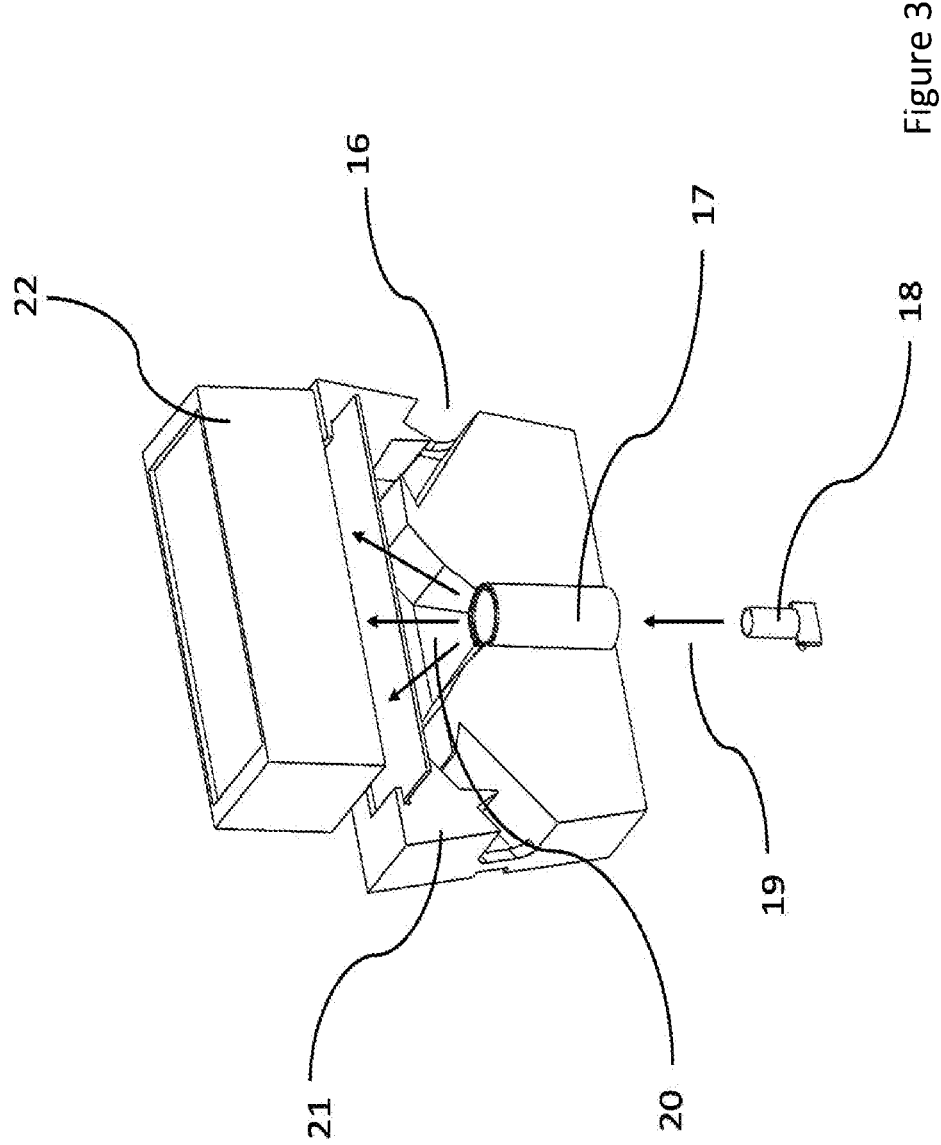
FIG. 3 is an exploded view of components of the airborne microbial growth and detection apparatus showing a located cartridge component relative to each of a light source and detector.
Figure 4:
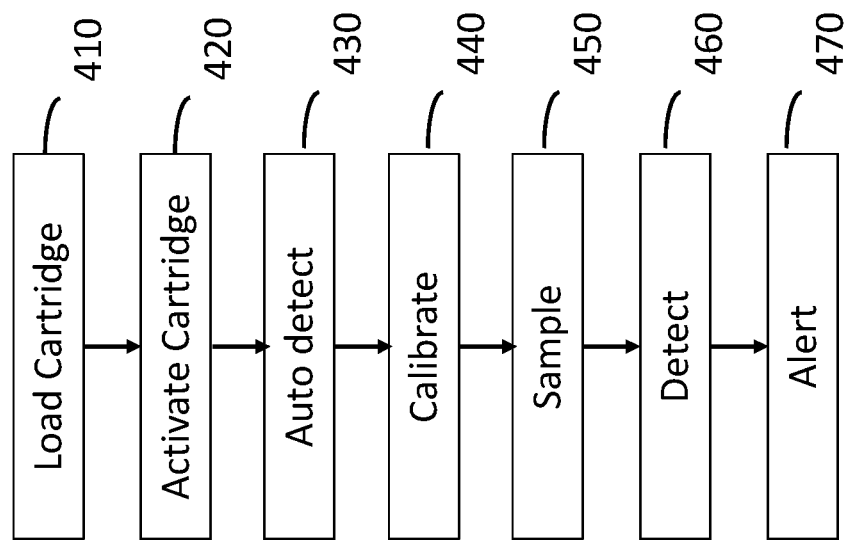
FIG. 4 is a detail of the sampling and monitoring method.

The present teachings relate to an assembly and method for capturing and proliferating airborne microbes and to remotely determine their presence by means of optical scattering and absorption of a collimated light source. While exemplary implementations and aspects of the present teaching will be described with reference to the accompanying drawings, it will be appreciated that the scope and spirit of the present teaching should not be construed as being limited in any fashion to the specifics now described which are illustrative of benefits associated with the present teaching and not intended to limit the present teaching to these specifics. Furthermore, where one or more elements are described with reference to one or more figures these could be replaced or used with one or more elements described with reference to other figures. For the purposes of the features that are described with reference to the accompanying figures the following reference numerals are used:

1—Cartridge protective glass cover (stops sedimentation of external microbes while loading)
2—Cartridge air inlet
3—Cartridge
4—Central unit (optics, electronics and fan)
5—Central unit air outlet
6—Cartridge guide rails
7—Positioning of optical electronics
8—Inlet for cartridge
9—Gravity assisted sedimentation area
10—Cartridge protective glass cover (stops sedimentation of external microbes while loading)
11—Cartridge air outlet
12—Cartridge
13—Nutrient media vial
14—Cartridge air inlet
15—Baffles to contain spores from hazardous growths
16—Cartridge air outlet
17—Nutrient media vial
18—Laser
19—Direction of light
20—Scattering of light as it passes through the detection area
21—Cartridge
22—Photodetector array for detection of transmitted/scattered light
Steps 410-470 exemplary process steps An exemplary aspect of a detection apparatus for detecting an airborne microbial growth in accordance with the present teaching is detailed in FIGS. 1 to 3. As is initially shown in FIG. 1, the present teaching provides a sterilized air sampling cartridge 3 which comprises a housing 100 within which is provided an integrated medium for selective growth of pathogens. The cartridge 3 is configured to be accurately aligned with and received through an inlet 8 for the cartridge into an interior volume of a central unit 4. Once located within the central unit, pathogens which are growing within the medium may be selectively detected. In this way the cartridge 3 forms an integral part of an in-situ monitoring system for the optical detection of the targeted pathogens.

As shown in FIG. 2, the growth medium is contained in a vial (13), as opposed to a Petri dish commonly used, which enables matching the area of the pathogen growth to the effective detection area, and reduces the amount of agar lost to evaporation.

The air sampling cartridge (3), containing a selective growth medium for targeted pathogens, is manufactured in a sterile environment, and sealed, so as to preserve sterility of the inner parts of the cartridge (including the growth medium) until deployment.

The air sampling cartridge 3 is designed to prevent exit of pathogens once they are detected. This is a key safety feature and is achieved disabling airflow through the cartridge via baffles and mechanically isolating the media in the cartridge from the external environment. As the vial is orientated in a vertical orientation with the mouth of the vial at the top of the vial, it will be appreciated that gravity also contributes to maintaining the pathogens within the vial.

The air sampling cartridge may be configured to incorporate one or more electronically readable identifiers such as those provided by proximity technologies: RFID, bar scanning, NFC, etc. This cartridge identification enables selective confirmation of the right medium, traceability of the sample, and re-testing for quality control.

The overall housing case, or central unit (4), is isolated from the air sampling cartridge, which keeps the system free of contamination and less prone to false signals. It will be appreciated that the pathogens are grown in a separate and distinct vial that is located within the removable cartridge. While this is locatable within the central unit and can be optically interrogated while located, the culture medium within the vial within which the pathogens grow is isolated from any air path within the interior volume of the central unit (4). This allows the central unit to be used in a plurality of different tests using different replaceable cartridges (3) without risk of cross contamination from detection of a sample pathogen in one cartridge with that of a sample pathogen in another cartridge.

The apparatus is configured to provide an assisted air path to facilitate the movement of air into the air sampling cartridge at the programmed intervals. Such assist may be provided by a fan. As shown in FIG. 2, as the vial 13 is located in a vertical orientation relative to the air path between the cartridge air inlet 14 and the cartridge air outlet 11, pathogens captured by the air will sediment under the influence of gravity (9) towards the growth medium provided within the vial.

The growth medium in the vial (13, 17) enables pathogen growth until a sufficient colony has developed, which can be detected by optical means. It will be appreciated that the induced air flow can be introduced from outside the housing into the interior volume where it is directed into the vial (13, 17) within which the growth media is located. The passage of air across the growth media effects the introduction of microbes from the ambient air external to the cartridge and apparatus generally onto the growth media where they can propagate and selectively culture in a fashion appreciated by those skilled in the art.

The vial (13, 17) is integrated with some of the optical elements (lenses and/or waveguides required to deliver the incident light over the entire growth area, and to optimize the detection onto the detecting elements.

As shown in FIG. 3, once the cartridge is received into the central unit, the vial (13, 17) is located in an optical path between a light source- suitably provided by a laser or high intensity LED which transmits light through the vial where it is then detected by a CCD array or similar detector (22). This light source is an example of a collimated light source. Based on the absorption and/or scattering of light arising from the level of pathogen growth within the vial, the transmitted and detected signal will vary and this variance can be used as an indication of the presence or otherwise of pathogen growth within the vial.

It will be appreciated that the detected signal pattern will provide an identifier for particular pathogen types and the levels of same. This can be calibrated using suitable calibration routines. This detection using a photodetector provided within the housing and located on an opposite side of the vial to the light source 18 ensures that light transmitted from the light source will pass through the container and impinge onto the detector. The level of microbial growth on the growth media will operably cause variations in the intensity of light that is transmitted along this optical path and will be sensed by the detector.

While not shown, the assembly may further comprise a second photodetector which is operably orientated relative to the vial to provide a measure of scattered light intensity from the microbial growth. This scattered light may be resultant from a forward scattering or a back scattering phenomena.

The light source 18 and the detectors 22 are desirably baffled such that ambient light external to the housing interior volume does not contribute to the light that is sensed by the photodetectors.

By providing the cartridge 3 as a removable element, it will be appreciated that an advantage of the current design allows for the growth media to be easily changed or replaced for consecutive measurements and that the growth media may be selective to particular microbial species.

The collimated light source in the preferred embodiment is a diode laser emitting in the red region of the electromagnetic spectrum; with wavelengths between approximately 620-750 nm.

Looking to the orientation of the baffle 15 in FIG. 2, it will be appreciated that the baffle is designed in such a way that as air is forced by an impeller, for example a fan, from left to right. The baffle and the lower surface of the optical slide 10 cause the air to change trajectory at an angle downwards in the vertical direction of the figure. The baffle forces the air together with airborne microbial particles drawn in from the impeller from a trajectory parallel to the open top of the vial (13, 17) to a trajectory angled downwards towards the growth media that is located within the vial. It may be appreciated that by means of a simple heating device, for example a heating coil, the growth media container may be kept at an elevated temperature suitable for the enhanced proliferation of certain microbes.

It will be appreciated and understood that the nature of the growth of microbial material within the vial will affect how the light from the collimated light source interacts with the microbial growth in the growth media. When the collimated light source is energized by a power supply collimated light passes into the vial in a direction parallel to a longitudinal axis of the vial. It will be appreciated by those skilled in the art that, as the collimated light passes through the microbial growth, the intensity of the light will be diminished along the path of transmission due to scattering and absorption and scattering of the light will take place off the collimated light path axis. A signal is produced by photodetector 22 with respect to the intensity of light along the path of transmission, while a second signal may also be produced by a non-identified photodetector with respect to the intensity of the light along the path of scattered light. The light path(s) may pass through an optical baffle, which serves to shield the photodetectors from ambient light sources and diminish light from reflections within the housing. Furthermore, the number of detectors may be increased to increase the amount of temporal and spatial information gathered concerning the absorption and scattering of the collimated light source by the microbial growth.

It is appreciated that by means of suitable electronic circuitry the signals produced by the optical detectors can be electrically transmitted from a transmitter to a remote receiver and stored for analysis by for example, a computing device.

FIG. 4 details the main steps in the process flow of the method of capturing and proliferating airborne microbes and determining their presence using the collimated light source. In step 410 a cartridge is loaded into the housing using the cooperating guide rails on each of the cartridge and the housing to secure accurate alignment of the two. This receipt of the cartridge can be used to trigger an activation of the unit (Step 420). This activation can be communicated to a user using an optical indicator such as an LED viewable on an exterior surface of the housing that will change color depending on the operating characteristic of the apparatus.

In Step 430, an auto-detect step is detailed. This can be effected through use of the readable identifiers provided on the cartridge and discussed above. Such detectors may allow identification of the cartridge type and the unit number which may be useful where a specific type of cartridge is useable for different types of pathogen detection or a series of cartridges of the same type are used for sequential analysis. It will be appreciated that an apparatus per the present teaching is configured to communicate with external computing resources and by tracing data to specific cartridges detailed analysis may be conducted on an on-going basis.

Having received and identified a cartridge type, the apparatus will typically execute a calibration routine (step 440) wherein parameters such as light intensity from the light source is identified and used to calibrate the detectors. A determination is made as to whether parameters such as transmission and scattering set values are met and in response gain or intensity values of the light source and/or detectors may be varied.

In Step 450, a detection or sampling routine is initiated. This will typically involve a periodic running of the assisted air flow to introduce new microbial matter into the vial at regular intervals. At the same time the light source may be operated in a pulsed fashion to regularly effect a signal analysis of the growth pattern of any pathogen within the vial. In this way an impeller, such as a fan, forces air together with airborne microbes into the cartridge via the dedicated air flow path that is isolated from the main housing components and on to the growth media located in the vial. It will be appreciated that by isolating the cartridge air flow path from the main housing components that while the cartridge may be located within a main body portion of the housing, that the air flow through the cartridge is isolated from the other components of the main housing components. In this way any microbial material that is conveyed in the air passing through the cartridge avoids contact with internal surfaces of the central unit (4) and therefore cannot contaminate or effect growth of microbial material on those surfaces. This allows the same central unit (4) to be used in a repeated fashion without requiring decontamination, disinfection or the like.

The microbial growth (if present) is illuminated with the collimated light source as previously described. The intensity of the light transmitted through the microbial growth is measured by the photodetector 22 (step 460). The intensity of the light scattered may also be measured by means of photodetectors. Signals are electronically transmitted to a remote receiver and stored; and the presence or the level of microbial growth is determined through analysis of measured signals.

In the event that a detected signal- or aggregation of a plurality of detected signals provides an indication of a trigger event, an alert (step 470) is activated. This alert can be implemented in a plurality of different mechanisms. For example a light indicator on the housing itself may be varied, a trigger notification response to an associated computing device may be provided. At this stage as the trigger condition is met, the influx of additional microbial material may be discontinued but monitoring of an already collected sample may continue.

It will be appreciated that the present teaching has been described with reference to preferred aspects and implementations but changes and modifications can be made without departing from the spirit or scope of the present teaching which should be limited only insofar as is deemed necessary in the light of the appended claims.

The words comprises/comprising when used in this specification are to specify the presence of stated features, integers, steps or components but does not preclude the presence or addition of one or more other features, integers, steps, components or groups thereof.

What is claimed is:

1. An airborne microbial growth and detection apparatus for detecting an airborne microbial growth, the apparatus comprising:
   a housing comprising a light source and a first detector, the housing having walls defining an interior volume configured to receive a removable cartridge, the cartridge having a vial defining a volume within which is provided a growth media substrate,
   the vial further comprising an open mouth through which air borne particles may pass into the volume of the vial and effect microbial growth on the growth media substrate, and
   wherein the cartridge and the housing are configured to mate with each other to effect an operable optical alignment of the vial in the received cartridge with each of the first detector and the light source, and
   wherein on receipt of the cartridge within the housing an air flow path through only the cartridge and past the open mouth of the vial is provided, the airflow path operably directing ambient air from outside the housing towards the growth media substrate to effect the microbial growth on the growth media substrate where it is operably detected through use of the light source and detector.

2. The apparatus of claim 1 comprising a sensor coupled to the first detector and configured to record intensity of light transmitted through the growth media substrate.

3. The apparatus of claim 2 comprising a transmitter configured to transmit information relating to microbial growth to a remote receiver.

4. The apparatus of claim 2 wherein the sensor is configured to compute, based on the recorded intensity, estimates of microbial growth.

5. The apparatus of claim 1 configured to relay information to the remote receiver on determination that the estimated microbial growth exceeds a predetermined parameter.

6. The apparatus of claim 3 configured to relay recorded intensities to the remote receiver.

7. The apparatus of claim 1 wherein the first detector is configured to detect light directly transmitted through the growth media.

8. The apparatus of claim 1 comprising a second detector configured to measure light scattered through the growth media.

9. The apparatus of claim 8 wherein the second detector is orientated or positioned relative to the growth media to operably detect light forward scattered through the growth media.

10. The apparatus of claim 8 wherein the second detector is orientated or positioned relative to the growth media to operably detect light back scattered through the growth media.

11. The apparatus of claim 1 comprising a heating device.

12. The apparatus of claim 1 comprising an impeller and a baffle, the impeller being located relative to the baffle to operably induce ambient air from external the housing into the housing.

13. A method for detecting airborne microbial growth comprising the steps of:
   providing a detection apparatus as set forth in claim 1;
   introducing a growth media substrate into the housing; and
   monitoring variances in the detected light levels through the substrate to provide an estimate of airborne microbial material.

* * * * *